US00PP08602P

United States Patent [19]

Suzuki

[11] Patent Number: Plant 8,602

[45] Date of Patent: Feb. 22, 1994

[54] ROSE PLANT KEIBELMI

[75] Inventor: Seizo Suzuki, Yachiyo, Japan

[73] Assignee: Bear Creek Gardens, Inc., Medford, Oreg.

[21] Appl. No.: 830,210

[22] Filed: Jan. 30, 1992

[51] Int. Cl.[5] ..... A01H 5/00

[52] U.S. Cl. ..... Plt./7.1

[58] Field of Search ..... Plt. 7.1, 10, 11, 12, Plt. 22, 29

*Primary Examiner*—Howard J. Locker
*Assistant Examiner*—E. F. McElwain
*Attorney, Agent, or Firm*—Klarquist, Sparkman, Campbell, Leigh and Whinston

[57] ABSTRACT

A new miniature rose created by crossing two unnamed varieties is characterized by its red and white bicolor flowers, its healthy, dark green, glossy and disease-resistant foliage, its abundance of flowers, its seven-leaflet leaves and its pleasant, light fragrance.

1 Drawing Sheet

The present invention relates to a new and distinct variety of rose plant of the miniature class which was originated by me by crossing an unnamed seedling with an unnamed seedling.

The primary objective of this breeding was to produce a new rose variety having the sharp bicolor contrast of the female unnamed seedling parent coupled with the abundant flowering vigorous growth, healthy foliage and miniature habit of the male unnamed seedling parent. The objective was substantially achieved along with other desirable improvements as evidenced by the following unique combination of characteristics which are outstanding in the new variety and which distinguish it from its parents, as well as from all other varieties of which I am aware:

1. A dwarf, miniature habit;
2. Healthy, mildew and rust resistant dark green glossy foliage;
3. Abundance of red and white bicolor flowers;
4. Seven leaflet leaves;
5. A pleasant light fragrance.

Asexual reproduction of this new variety by softwood cuttings, as performed at Wasco, Calif., shows that the foregoing characteristics and distinctions come true to form and are established and transmitted through succeeding propagations.

The accompanying photograph shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling.

*Pollen parent.*—Unnamed seedling.

Classification:

*Botanical.*—*Rosa hybrida.*

*Commercial.*—Miniature.

FLOWER

Observations made from specimens grown in a garden environment in Somis, Calif.

Blooming habit: Continuous.

Bud:

*Size.*—¾" when the petals start to unfurl.

*Form.*—Short, pointed ovoid.

*Color.*—When sepals first divide, bud color is White Group 155B at the petal base. The bud color changes to Red Group 45D at the top three-quarters of the outer or guard petals of the bud. When half blown, the upper sides of the petals are Red Group 45A; except for the outer or guard petals, the lower sides of the petals are White Group 155B. These petals give the appearance of having a light pink color that is most evident toward the petal edges; however, this pink color is not actually on the petal reverse, but is a bleeding-through of the color from the upper side through the translucent white lower side of the petal. Upon peeling of the petal, the lower side evidences no pink color.

*Sepals.*—Color: Green group 139D. Surface texture: Covered in fine hairs. There are three lightly appendaged sepals. There are two unappendaged sepals with hairy edges.

*Receptacle.*—Color: Green group 137C. Shape: Funnel. Size: Small, ¼"×¼". Surface: Smooth.

*Peduncle.*—Length: Short, 1½". Surface: Smooth, with a few small glands. Color: Medium green. Strength: Stiff, erect, slender.

Bloom:

*Size.*—Small. Average open size is 2 inches.

*Borne.*—Several together, in flat clusters of 5 to 10 flowers. A cluster opens with the central flower, and within 2 or 3 days, the remaining flowers of a cluster open in no particular sequence.

*Stems.*—Short, strong, 6" long.

*Form.*—When first open: High centered. Permanence: Flattens.

*Petalage.*—Number of petals under normal conditions: 25.

*Color.*—The upper side of the petals is Red Group 45A. The reverse side of the petals is White Group 155B. The base of the petals have a small white half moon ¼" high by 3/8" wide. The major color on the upper side is Red Group 45A.

*Variegations.*—None.

*Discoloration.*—The general tonality at the end of the first day: No change. At the end of the third day: The red color darkens toward Red Group 46A.

*Fragrance.*—Moderate.

Petals:

*Texture.*—Thick.

*Shape.*—Deltoid.

*Form.*—Flat.

*Arrangement.*—Imbricated, with a few petaloids in the center.

*Persistence.*—Drop off cleanly.

*Lastingness.*—On the plant: Long, 5-6 days. As a cut flower: Long, 7 days.

Reproductive parts:

*Anthers.*—Size: Medium. Quantity: Many. Color: Yellow. Arrangement: Regular around styles, mixed with occasional petaloids.

*Filaments.*—Color: Yellow.

*Pollen.*—Color: Gold-yellow.

*Styles.*—Color: Red.

*Stigmas.*—Color: Greenish-white.

Form: Bush.

Growth: Vigorous, upright, branching, dwarf, 30 inches; in height at one year of age.

Foliage: Number of leaflets on normal mid-stem leaves: 7.

*Size.*—Small, 3½" long×2" wide.

*Quantity.*—Abundant.

*Color.*—New and old foliage: Green Group 147A.

Leaflets:

*Shape.*—Pointed oval.

*Texture.*—Upper side: Leathery, glossy.

*Edge.*—Serrated.

*Serration.*—Single, small.

*Petiole rachis.*—Color: Reddish.

*Petiole underside.*—Smooth, with occasional small prickles.

*Stipules.*—Medium ¾", smooth.

*Disease resistance.*—Resistant to mildew and rust under normal growing conditions at Somis, Calif.

Wood:

*New wood.*—Color: Reddish. Bark: Smooth.

*Old wood.*—Color: Green. Bark: Smooth.

Prickles: Thorns.

*Quantity.*—On main canes from base: Ordinary. On laterals from main canes: Ordinary.

*Form.*—Medium, straight.

*Color when young.*—Red.

*Color when mature.*—Brown.

*Length when mature.*—⅛ to 3/16 inches.

Small prickles:

*Quantity.*—On main stalks: None. On laterals: None.

I claim:

1. A new and distinct variety of rose plant of the miniature class, substantially as herein shown and described, characterized particularly as to novelty by the unique combination of its distinctive red and white bicolor flowers, its healthy dark green, glossy and disease-resistant foliage, its abundance of flowers, its dwarf miniature habit of growth, its seven leaflet leaves and its pleasant, light fragrance.

* * * * *

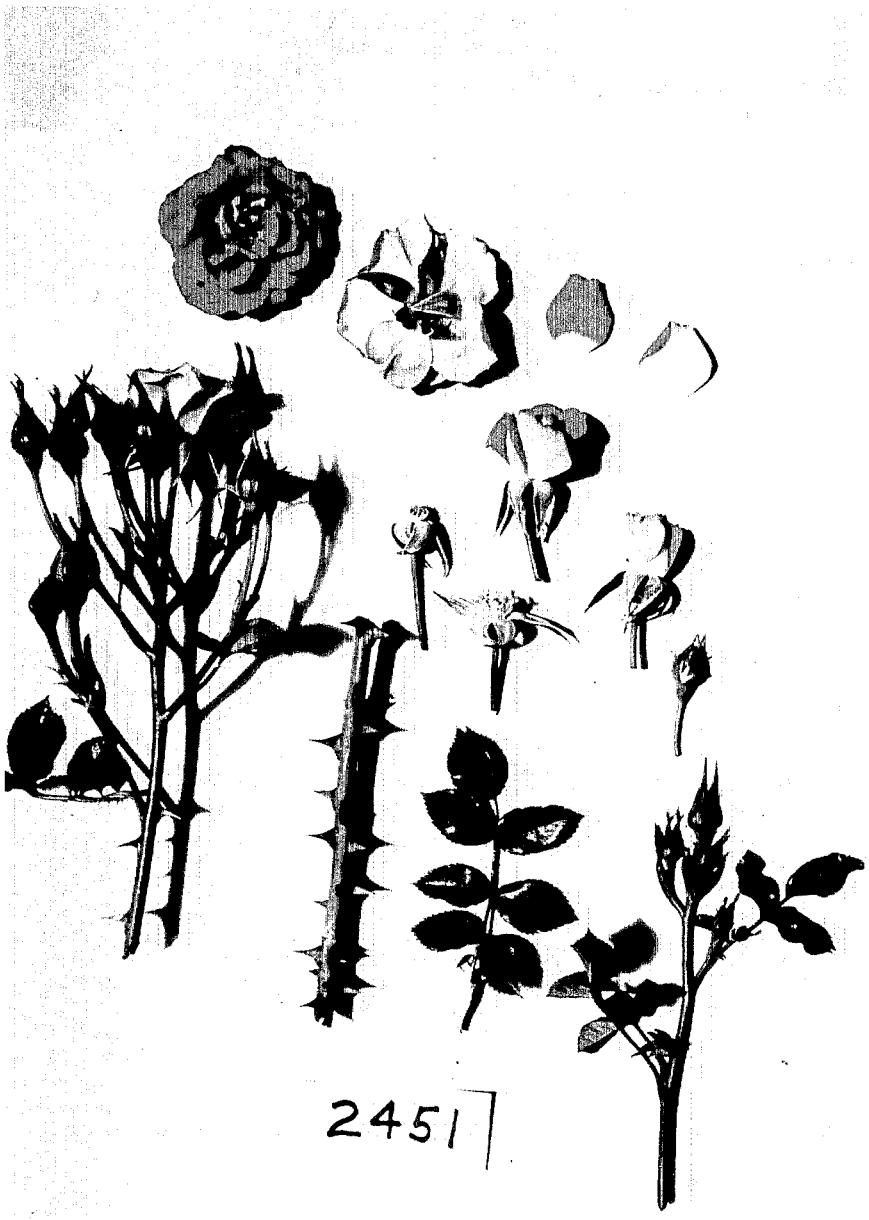
2451